United States Patent [19]

Reichstein et al.

[11] Patent Number: 4,773,394
[45] Date of Patent: Sep. 27, 1988

[54] UPPER GASTROINTESTINAL ENDOSCOPE INTUBATOR

[76] Inventors: Irving P. Reichstein, 2970 N. Lake Shore Dr., Apt. 19B/C, Chicago, Ill. 60657; Benjamin J. Reichstein, 2721 Lincoln La., Wilmette, Ill. 60091

[21] Appl. No.: 108,117

[22] Filed: Oct. 14, 1987

[51] Int. Cl.⁴ .................. A61B 1/00; A61M 25/02
[52] U.S. Cl. .......................... 128/4; 604/54; 604/161; 604/171
[58] Field of Search ............... 128/3, 4, 5, 6; 604/49, 604/54, 160, 161, 171, 172

[56] References Cited

U.S. PATENT DOCUMENTS

| 3,941,119 | 3/1976 | Corrales | 604/49 X |
| 4,175,564 | 11/1979 | Kwak | 604/54 X |
| 4,580,556 | 4/1986 | Kondur | 128/4 X |
| 4,687,470 | 8/1987 | Okada | 604/171 |

Primary Examiner—William H. Grieb
Attorney, Agent, or Firm—Wallenstein, Wagner, Hattis & Strampel, Ltd.

[57] ABSTRACT

A novel endoscopic intubator which permits atraumatic intubation through the cricopharyngeal sphincter of the esophagus without risk of perforation of the esophagus or pharynx. The intubator of the present invention comprises a deformable hood for shielding and carrying the distal end of the endoscope, the hood having two deformable leaves which define a pocket for receiving the distal end, an elongaed conduit joined to the hood for external manipulation of the hood, the length of conduit being at least coextensive with the length of the shaft of the endoscope so that a proximal end of the conduit protrudes from the patient's mouth, and an annular gripping member secured to the proximal end of the conduit to permit an endoscopist to slidably withdraw the hood from the distal end.

11 Claims, 2 Drawing Sheets

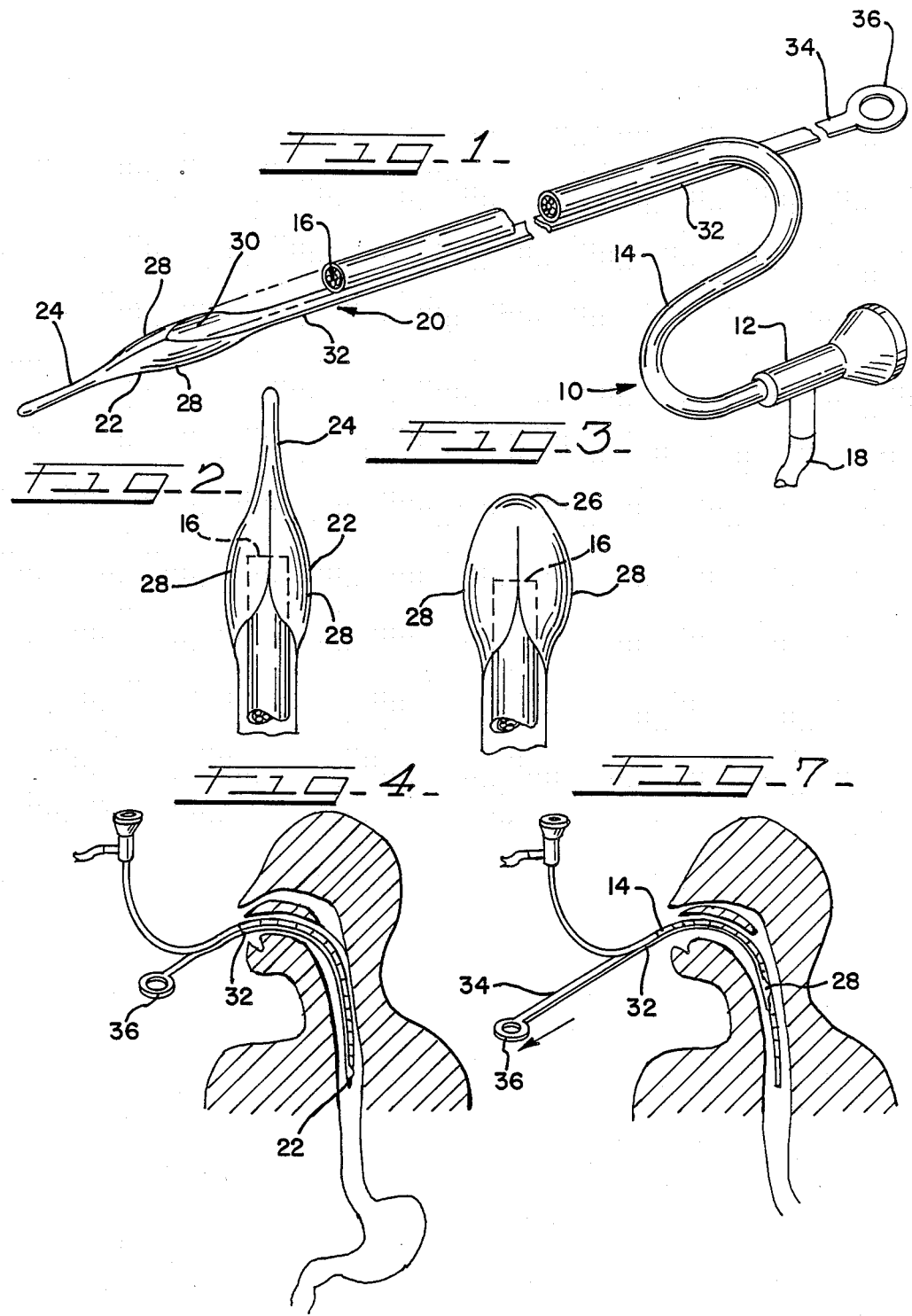

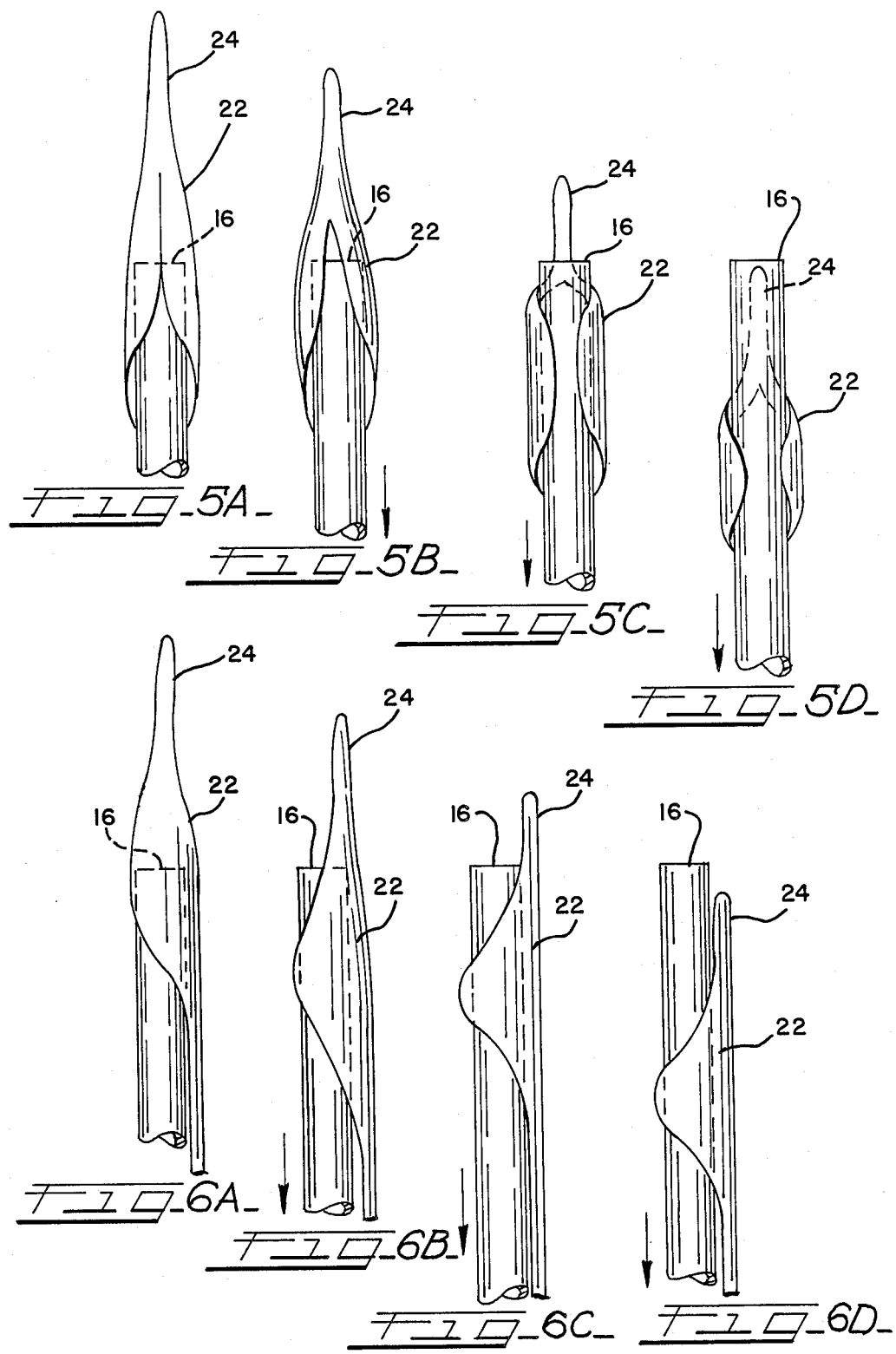

UPPER GASTROINTESTINAL ENDOSCOPE INTUBATOR

DESCRIPTION

TECHNICAL FIELD OF THE INVENTION

The present invention generally relates to apparatuses and methods for intubation of the upper gastrointestinal tract of humans for diagnostic or therapeutic purposes, and in particular, to a device to enable the intubation of the upper gastrointestinal tract with a fiberoptic or video flexible endoscope.

BACKGROUND OF THE INVENTION

Esophago-gastro-duodenoscopy is a routine outpatient procedure which permits the direct observation, biopsy, and photography of pathological processes in the esophagus, stomach or duodenum. Duodenoscopy with cannulation and radiopaque dye injection of the common bile duct and pancreatic duct enable visualization and diagnosis of pathological processes of these organs. Therapeutic endoscopy permits (1) the control of bleeding from upper gastrointestinal sources utilizing techniques of injection of sclerosant, electrocautery, application of heater probe or laser, (2) the removal of neoplastic growths, and (3) the relief of obstructing pathological process by intubation or ablative procedures. Endoscopy requires motivation, dexterity, and experience. Patients may suffer when examinations are not properly performed.

There are three basic methods for passing the flexible endoscope. See Cotton & Williams, *Practical Gastrointestinal Endoscopy*, Blackwell Scientific Publications, (2d ed. 1982), p. 24-27. For all methods the patient is positioned in the left lateral decutibus position and is administered intravenous sedation and topical anesthesia to the mouth and pharynx.

(1) With mouthguard in place, the endoscopist passes the instrument tip through the mouthguard and over the tongue to the back of the mouth; the tip of the instrument is deflected in the midline over the back of the tongue and into the middle of the pharynx. The tip is advanced and the patient is asked to swallow to relax the cricopharyngeal sphincter, which lies 15-18 cm from the incisor teeth. Passage of the tip of the instrument is felt as resistance is lost. If the tip does not pass after two or three swallows, it is probably not in the midline and it should be withdrawn and repositioned.

(2) The instrument is passed through the mouthguard and over the back of the tongue into the pharynx as in method 1. The objective lens is brought to the eye of the endoscopist, and the tip of the instrument is advanced over the back of the tongue under direct vision. The patient is asked to swallow and the tip of the instrument is advanced through the sphincter under direct vision.

(3) The endoscopist passes the tip of the instrument over the tongue using the inserted fingers of his left hand to guide it into the midline of the pharynx. The patient is asked to swallow after the fingers are withdrawn and the mouthguard is placed. If swallowing is not effective, the tip of the instrument has probably fallen into the left pyriform fossa, and it may be necessary to reinsert a finger to lift the tip of the instrument back into the midline.

These methods of insertion are easier with small instruments of narrow diameter and with lateral-viewing endoscopes which have a smooth, rounded tip. Newer diagnostic and therapeutic endoscopes are of larger diameter, however, to accommodate extra channels for suction, biopsy, and laser.

In each intubation method, the most difficult and dangerous point in passing the endoscope is traversing the cricopharyngeal sphincter. The three methods above rely on the swallowing maneuver to relax this muscular sphincter and permit the endoscope to pass. There is critical dependence on the cooperation of the patient. Repeated forceful attempts to pass the endoscope through a contracted cricopharyngeal sphincter may lead to perforation of the esophagus or pharynx. The passage of the endoscope in patients who are not able to cooperate is dangerous and requires great skill on the part of the endoscopist.

Hence, prior to the present invention, a need existed for a safe technique to pass the endoscope through the cricopharyngeal sphincter with reduced risk of perforation of the esophagus or pharynx.

SUMMARY OF THE INVENTION

According to the present invention, a novel endoscopic intubator has been developed which permits intubation of an endoscope through the cricopharyngeal sphincter without risk of perforation of the esophagus or pharynx. After safe intubation, the intubator of the present invention may be removed from the endoscope and withdrawn through the patient's mouth leaving the endoscope in position for continuation and completion of the endoscopic procedure.

Generally, the intubator of the present invention includes a flexible hood for carrying and shielding a distal end of an instrument or diagnostic shaft of an endoscope. The hood comprises at least two deformable leaves which define a pocket for receiving the shaft of the endoscope. Joined to the hood is an elongated control means, preferably a conduit for externally manipulating the hood upon intubation of the endoscope shaft. The length of the control conduit is at least coextensive with the length of the endoscope shaft so that a proximal end of the control conduit protrudes from the patient's mouth. Attached to the proximal end of the control conduit is a gripping means, preferably an annular member which permits an endoscopist to slidably move the intubator along the endoscope shaft after intubation within a patient.

The intubator of the present invention is used by inserting the distal end of the endoscope shaft into the pocket of the hood. Next the intubation procedure is performed until approximately 20 cm. of the endoscope shaft has been passed as measured from the incisors. At such point, the distal end of the endoscope shaft, shielded by the hood, normally should have passed through the cricopharyngeal sphincter. After achieving such positioning, the endoscopist begins drawing on the control conduit in an orad direction while maintaining the endoscope shaft stationary. Such orad directional movement draws the hood against the distal end of the endoscope shaft causing a gradual retraction and deformation of the leaves of the hood thereby exposing the distal end. Continued orad directional movement results in complete removal of the intubator from the patient at which point the endoscopic procedure may be continued.

The intubator of the present invention permits atraumatic intubation of an endoscope in all patients, including those who are not capable of cooperation. Use of the present invention may permit upper gastrointestinal endoscopy to be performed with less intravenous sedation, and thereby, with less risk of aspiration.

Other advantages and aspects of this invention will become apparent upon making reference to the specification, claims, and drawings to follow.

BRIEF DESCRIPTION OF THE DRAWINGS

FIG. 1 is an exploded perspective view of an endoscope and one embodiment of the intubator of the present invention prior to insertion of a distal end of the endoscope within the intubator;

FIG. 2 is a fragmented top view of one embodiment of the hood of the intubator of the present invention;

FIG. 3 is a fragmented top view of another embodiment of the hood of the intubator of the present invention;

FIG. 4 is a perspective view illustrating intubation of an endoscope through use of the intubator of the present invention;

FIGS. 5A through 5D are fragmented top views of the hood disclosing deformation of the leaves of the hood upon orad directional movement of the present invention;

FIGS. 6A through 6D are side views of each of the views of FIGS. 5A through 5D; and, FIG. 7 is the same perspective view of FIG. 4 disclosing withdrawal of the intubator of the present invention through orad directional movement.

DETAILED DESCRIPTION OF PREFERRED EMBODIMENTS

While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention the embodiment illustrated.

Referring now to the drawings, FIG. 1 generally discloses a simple gastrointestinal endoscope 10 having an eyepiece 12 optically coupled to an elongated and flexible instrument shaft 14 having a distal end 16 which permits viewing and operative access to the surgical field. Typically connected at or near eyepiece 12 is a multi-functional conduit providing light and fluid sources to shaft 14.

FIG. 1 also discloses a preferred embodiment of an intubator of the present invention, generally referenced by 20. Intubator 20 comprises a hood portion 22 for shielding and carrying the distal end 16 of the instrument shaft 14. All embodiments of intubator 22 disclosed in FIGS. 1 and 2 feature an outer contour and configuration which functions to permit atraumatic passage of the distal end 16 of endoscope 14 through the esophagus and in particular through the cricopharyngeal sphincter. The preferred embodiment of hood portion 22 disclosed in FIGS. 1 and 2 utilizes an elongated tapered guide tip 24 for effecting atraumatic contact with esophageal tissue. Another embodiment of hood portion 22 disclosed in FIG. 2 utilizes a parabolic-shaped end 26 foreffecting atraumatic passage of the intubator 20 through the esophageal lumen.

All embodiments of hood portion 22 are manufactured from shape retentive yet deformable, biologically inert material such as medical grade silicon, latex rubber or red rubber. Deformability of hood portion 22 is required not only to achieve atraumatic intubation of intubator 20, but also is necessary for orad withdrawal of the intubator upon passage through the cricopharyngeal sphincter.

For example, all embodiments of hood portion 22 are comprised of a plurality of deformable leaves 28, but preferably two leaves 28, which define a pocket 30 in which is inserted and carried the distal end 16 of instrument shaft 14 as shown in FIGS. 2 and 3. Pocket 30 has inner dimensions generally corresponding to the outer dimensions of the distal end 16 of the endoscope 10 so that the distal end may be securely carried within hood portion 22, yet permits slidable movement of the distal end within the pocket 30 upon orad movement of the intubator 10. The withdrawal of intubator 10 from a patient upon intubation through the cricopharyngeal sphincter and the operation of leaves 28 to permit release of distal end 16 from pocket 30 will be explained later in greater detail.

As best disclosed in FIG. 1 hood portion 22 is joined to a hood portion control means, preferably an elongated conduit 32. The length of the control conduit 32 is at least coextensive with the length of the instrument shaft 14 of the endoscope 10. Such length of conduit 32 allows a proximal end 34 to protrude from the patient's mouth as disclosed in FIGS. 4 and 7. Secured to the proximal end 34 of the control conduit 32 is a gripping means, preferably an annular member 36. Through use of annular member 36 an endoscopist may slidably move the intubator in an orad direction along the instrument shaft 14. Because the control conduit 32 will be drawn upon by the endoscopist, it is important that the control conduit be manufactured from a generally non-elastic, but biologically inert material such as medical grade polyvinylchloride or polyurethane.

The intubator of the present invention is used by inserting the distal end 16 of the instrument shaft 14 into the pocket 30 of the hooded portion 22 prior to initiating intubation as shown in FIGS. 5A and 6A. Next the intubation procedure is performed so that the control conduit 32 remains closely juxtaposed to the instrument shaft 16 and proximal end 34 of the control conduit 32 trails out of the patient's mouth as disclosed in FIG. 4. The intubation continues until approximately 20 cm. of the shaft 16 has been intubated, as measured from the incisors. At this point, for most patients, the distal end 16 of the endoscope 10, as shielded by hooded portion 22 should have passed the cricopharyngeal sphincter.

If this has been achieved, then the endoscopist may grasp the annular member 36 and begin slowly drawing on the control conduit 32 in an orad direction to begin the process of withdrawing the intubator from the endoscope and out of the patient. Such orad directional movement of the intubator forces the distal end 16 forward in the pocket 30 causing the outer contour and configuration of the hooded portion to distort so that the leaves 28 begin to spread open as disclosed in FIGS. 5B and 6B.

As orad directional movement of the intubator continues, more of distal end 16 continues to be exposed as the leaves 28 begin to wrap around the circumference of the instrument shaft 14 as best seen in FIGS. 5C and 6C. Continued orad withdrawal of the intubator in the manner disclosed in FIG. 7 results in complete exposure of the distal end 16 and is concluded upon removal of the intubator from the patient. After removal of the intubator, the endoscopic procedure may be continued. Use of the intubator of the present invention allows for safe and atraumatic intubation of either a diagnostic or operative endoscope. Because the intubator of the present invention minimizes patient discomfort during intubation, less intravenous sedation is required with a corresponding reduction in the risk of aspiration.

While the invention has been described with reference to a preferred embodiment, it will be understood by those skilled in the art that various changes may be made and equivalents may be substituted for elements thereof without departing from the broader aspects of the invention.

We claim:

1. A device for facilitating intubation of a distal end of a shaft of an endoscope within the upper gastrointestinal tract, comprising:

a hood for shielding and carrying the distal end of the endoscope, the hood having a pocket for receiving the distal end of the endoscope, the pocket being defined by a plurality of deformable leaves, the pocket having inner dimensions generally corresponding to the outer dimensions of the distal end of the endoscope; and, an elongated hood control means joined to the hood for external manipulation of the hood, the length of the control means being coextensive with at least the length of the shaft so that a proximal end of the control means may protrude out of a patient's mouth;

such that an endoscopist may insert the hood on the shaft by seating the distal end within the pocket, upon intubating the shaft and achieving selected positioning of the shaft within the esophagus the endoscopist draws on the proximal end of the control means while maintaining the shaft in a stationary position to cause movement of the hood along the shaft in an orad direction, such orad directional movement of the hood causes the leaves to deform and retract thereby opening the pocket and exposing the distal end, continued drawing on the control means in the orad direction causes a complete withdrawal of the hood from the distal end of the shaft.

2. The device of claim 1 wherein at least the hood is made from shape retentive, deformable and biologically inert material.

3. The device of claim 2 wherein said material may be selected from the group consisting of silicon, red rubber and latex rubber.

4. The device of claim 1 wherein a distal end of the hood includes a guide tip for deflecting and parting esophageal tissue.

5. The device of claim 4 wherein the guide tip includes an elongated generally tapered end.

6. The device of claim 4 wherein the guide tip includes a parabolic shaped end.

7. The device of claim 1 wherein said hood control means includes a conduit generally conforming to the circumference of the shaft of the endoscope.

8. The device of claim 7 wherein said conduit is made from a biologically inert non-extendable material.

9. The device of claim 1 wherein the proximal end of the hood control means includes a gripping means.

10. The device of claim 9 wherein the gripping means includes an annular member.

11. A method of atraumatic intubation of a distal end of an endoscope in the upper gastrointestinal tract comprising the steps of:

shielding the distal end in deformable hood means;

intubating the shielded distal end within the esophagus until such point that the distal end of the endosco traverses the cricopharyngeal sphincter;

withdrawing the deformable hood means from the distal end of the endoscope; and, removing the deformable hood means from the patient.

* * * * *